United States Patent [19]

Coombes et al.

[11] Patent Number: 5,397,572
[45] Date of Patent: Mar. 14, 1995

[54] RESORBABLE MATERIALS BASED ON INDEPENDENTLY GELLING POLYMERS OF A SINGLE ENANTIOMERIC LACTIDE

[75] Inventors: Allan G. A. Coombes; James D. Heckman; Barbara D. Boyan, all of San Antonio, Tex.

[73] Assignee: Board of Regents, The Univeristiy of Texas System, Austin, Tex.

[21] Appl. No.: 162,633

[22] Filed: Dec. 2, 1993

Related U.S. Application Data

[60] Division of Ser. No. 528,968, May 24, 1990, abandoned, and a continuation of Ser. No. 914,992, Jul. 16, 1992, Pat. No. 5,290,494, which is a continuation of Ser. No. 528,968, May 24, 1990, abandoned, which is a continuation-in-part of Ser. No. 489,078, Mar. 5, 1990, abandoned.

[51] Int. Cl.$^6$ ............................ C08J 9/28; A61F 2/00; B32B 3/26
[52] U.S. Cl. ................................. 424/426; 428/220; 428/315.7; 521/64; 521/134; 521/182; 521/189; 525/413; 528/354
[58] Field of Search .................. 521/64, 134, 182, 189; 525/413; 528/354; 428/220, 315.7; 424/426

[56] References Cited

U.S. PATENT DOCUMENTS

| | | | |
|---|---|---|---|
| 4,471,077 | 9/1984 | Lange .................................. | 521/64 |
| 4,550,449 | 11/1985 | Tunc . | |
| 4,563,489 | 1/1986 | Urist . | |
| 4,578,384 | 3/1986 | Hollinger . | |
| 4,637,931 | 1/1987 | Schmitz . | |
| 4,645,503 | 2/1987 | Lin et al. . | |
| 4,719,246 | 1/1988 | Murdoch et al. ..................... | 521/64 |
| 4,776,329 | 10/1988 | Treharne . | |
| 4,781,183 | 11/1988 | Casey e al. . | |
| 4,792,336 | 12/1988 | Hlavacek et al. . | |
| 4,800,219 | 1/1989 | Murdoch et al. ..................... | 525/413 |
| 5,290,494 | 3/1994 | Coombes et al. ..................... | 264/41 |

FOREIGN PATENT DOCUMENTS 2215209A  4/1989  United Kingdom .

OTHER PUBLICATIONS

Hollinger, et al., "Biodegradable Bone Repair Materials. Synthetic Polymers and Ceramics", *Clin. Orthop. Rel. Resl.*, No. 207, pp. 290–305 (1986).

Hollinger, "Preliminary report on the osteogenic potential of a biodegradable copolymer of polyactide (PLA) and polyglycolide (PGA)" *J. Biomed. Mater. Res.*, vol. 17, pp. 71–82 (1983).

Higashi, et al., "Polymer–hydroxyapatite composites for biodegradable Bone fillers", *Biomaterials*, vol. 7, pp. 183–187 (1986).

Schmitz, et al., "A Preliminary Study of the Osteogenic Potential of a Biodegradable Alloplastic-Osteoinductive Alloimplant", *Clin. Orthop. Rel. Res.*, No. 237, pp. 245–255 (1988).

Kulkarni, et al., "Polylactic Acid for Surgical Implants", *Arch. Surg.*, vol. 93, pp. 839–843 (1966).

Getter, et al., "A biodegradable intraosseous appliance in the treatment of mandibular fractures", *J. Oral Surg.*, vol. 30, pp. 344–348 (1972).

Leenslag, et al., "Resorabable materials of poly(L–lactide). VI. Plates and screws for internal fracture fixation", *Biomaterials*, vol. i, pp. 70–73 (1987).

(List continued on next page.)

*Primary Examiner*—Morton Foelak
*Attorney, Agent, or Firm*—Anold, White & Durkee

[57] ABSTRACT

Resorbable materials and their preparation based on gelling a solution of a single polylactide enantiomer. The gel may be dried to produce solid materials, or may be extracted with a nonsolvent prior to drying to make microporous materials. Physical and mechanical properties of the material may be varied by varying the molecular weight of the gelling polymer, or by blending the gelling solution with other polymers or fillers. The resorbable materials can be used to make biodegradable implantation devices.

19 Claims, 1 Drawing Sheet

OTHER PUBLICATIONS

Bostman, et al., "Biodgradable Internal Fixation For Malleolar Fractures A Prospective Randomised Trail", *J. Bone and Joint Surgery*, vol. 69-B, No. 4, pp. 615-619 (1987).

Reul, "Use of Vicryl (Polyglactin 910) Sutures in General Surgical and Cardiothoracic Procedures", *Ann. J. Surg.*, vol. 134, pp. 297-299 (1977).

Greisler, "Arterial Regeneration Over Absorbable Prosthesis", *Arch. Surg.*, vol. 117, pp. 1425-1431 (1982).

Schakenraad, et al., "Biodegradable hollow fibres for the controlled release of drugs", *Biomaterials*, vol. 9, pp. 116-120 (1988).

Goldstrohm, et al., "The Results of 39 Fractures Complicated by Major Segmental Bone Loss and/or Leg Length Discrepancy", *J. Trauma*, vol. 24 No. 1, pp. 50-58 (1984).

Osborn, et al., "Bonding Osteogensis Induced by Calcium Phosphate Ceramic Implants", Biomaterials, pp. 51-58 (1980).

Holmes, et al., "A Coralline Hydroxyapatite Bone Graft Substitute", *Clin. Orthop. Rel. Res.*, No. 188, pp. 252-262 (1984).

Kelly, et al., "Totally Resorbable High-Strength Composite Materials", *Advances in Biomedical Polymers*, pp. 75-85 (1987).

Cutright, et al., "The repair of fractures of the orbital floor using biodegradable polylactic acid", *Oral Surg.*, vol. 33, No. 1, pp. 28-34 (1972).

Tunc, et al., "Body Absorbable Osteosynthesis Devices", *Advances in Biomedical Polymers*, pp. 87-99 (1987).

Christel, et al., "Biodegradable Composites for Internal Fixation" *Biomaterials*, pp. 271-280 (1980).

Offergeld, et al., "The Injection Molding of Resorbable Implants" ANTEC Abstracts, (1989).

Hollinger et al., "An evaluation of two configurations of tricalcium phosphate or treating craniotomies," J. Biomed. Mater. Res., vol. 23, pp. 17-29.

RESORBABLE MATERIALS BASED ON INDEPENDENTLY GELLING POLYMERS OF A SINGLE ENANTIOMERIC LACTIDE

This is a divisional of application Ser. No. 07/528,968, filed May 24, 1990, now abandoned. This is also a continuation of copending application Ser. No. 07/914,992, filed Jul. 16, 1992, which is a file wrapper continuation of application Ser. No. 07/528,968, filed May 24, 1990, now abandoned, which was a continuation-in-part of application Ser. No. 07/489,078, filed Mar. 5, 1990, now abandoned.

BACKGROUND OF THE INVENTION

1. Field of the Invention

This invention relates to resorbable materials made by gelling a solution of a single polylactide enantiomer. Such materials can be used to make resorbable implantation devices of designed morphology and thickness.

2. Description of Related Art

The poly alpha-hydroxy acids are a class of synthetic aliphatic polyesters, the main polymers of which are polylactide (alternatively referred to as polylactic acid) and polyglycolide (alternatively referred to as polyglycolic acid). These materials have been investigated for use in a variety of implant systems for soft tissue and osseous repair in medicine and dentistry, since they tend to exhibit very good biocompatibility and are biodegradable in vivo. The need to remove the device after tissue repair can thereby be reduced or eliminated. The alpha-hydroxy acids are also being investigated for production of controlled release rate delivery systems for bioactive materials, such as pharmaceuticals.

The repair of osseous defects, such as developmental malformations and surgical resections, has stimulated development and application of a wide range of synthetic and natural bone repair materials or bone substitutes. Iliac crest autograft has been shown to be an effective graft material (See, for example, Goldstrohm et al., J. Trauma., 24:50–58, 1984), but the supply is limited, requiring, in some cases of segmental defect repair or tumor resorption, multiple procedures to obtain sufficient material. In addition, the removal of cancellous graft can create additional surgical trauma, increase the potential for infection, and, by lengthening the operating time, increase the risk.

These disadvantages have spurred investigations of alternative bone repair materials. Bioceramics of calcium phosphate have attracted widespread attention because of their biocompatibility and chemical similarity to the bone matrix, which results in direct bonding to bone without intervening fibrous tissue (See, Osborn et al., Biomaterials, Winter, Gibbons, Plenk (eds.), 1980). However, they tend to be brittle, difficult to shape, and remain in the repair for time periods greater than 12 months (See, Holmes et al., Clin. Orthop. Rel. Res., 188:252–62, 1984).

The ability to vary the biodegradation rate of synthetic alpha-polyesters by material selection, copolymerization, control of molecular weight, crystallinity and morphology makes them attractive for bone repair. Resorption rate can be varied from two weeks to over a year, for example, so that implant resorption may be tuned to bone repair rates (See, Hollinger et al., Clin. Orthop. Rel. Res., 207:290–305, 1986). PLA/PGA copolymers have been used alone (Hollinger, J. Biomed. Mater. Res., 17:71–82, 1983) and as binders for bioceramics (Higashi et al., Biomaterials, 7:183–87, 1986) and decalcified allogeneic bone (Schmitz et al., Clin. Orthop. Rel. Res., 237:245–55, 1988) to produce bone fillers for repairing bony deficiencies in animals.

Such polymers can also function as delivery systems for growth factor(s) as they tend to biodegrade. U.S. Pat. No. 4,578,384 discloses a protein-acidic phospholipid addition to PLA/PGA copolymer which is reported to increase bone healing rates in rat tibias relative to the copolymer. PLA could, in itself, play a dual role of bone filler and bone growth factor. Hollinger, J. Biomed. Mater. Res., 17:71–82 (1983), reported that a 50:50 copolymer of poly(L-lactide coglycolide) increased the rate of early osseous healing when implanted in rat tibial defects. Thus, it appears that the degradation products of these linear aliphatic polyesters may play a role in the stimulation of hard and soft tissue growth, which increases the attraction of using PLA and PGA for repairing soft or hard tissue.

Metal internal fracture fixation plates, produced for example from stainless steel, frequently have an elastic modulus greater than ten times that of bone. Although plate rigidity is an advantage for achieving primary osseous union, it tends to inhibit external callus formation, which is considered a good method for restoring the strength of the broken bone to its original level (See, Kelley et al., Advances in Biomedical Polymers, Gebelein, C.G. (ed.), Plenum Press:New York, 1987). Active remodeling of the bone after fracture healing may also be compromised unless the rigid plate is removed, often resulting in stress protection and, consequently, osteoporosis and atrophy beneath the plate.

The potential advantages of internal fixation devices produced from biodegradable polymers have long been recognized. Primary bony union and callus formation could be achieved by an adequately stiff and strong plate. Load transfer to the healing bone and bone remodeling may be promoted by a gradually reducing plate stiffness as biodegradation proceeds. Finally, the need for plate removal may be eliminated by resorption of the device.

Kulkarni et al., Arch. Surg., 93:839–43 (1966), describe the production of poly(DL-lactic acid) pins for reduction of mandibular fractures in dogs. Getter et al., J. Oral Surg., 30:344–48 (1972), describe the use of high molecular weight PLA plates to treat mandibular fractures in dogs. Leenslag et al., Biomaterials, 8:70–73 (1987), disclose treatment of fractured zygoma in 10 patients using high molecular weight PLA plates. Such polymers, however, tend to be absorbed very slowly. Bostman et al., J. Bone and Joint Surgery, 69-B, No. 4 (1987), describe the use of high strength, fast resorbing, self-reinforced PLA/PGA rods for routine treatment of patients with displaced malleolar fractures.

Soft tissue repair has been a major area of application for synthetic biodegradable polymers. Reul, Ann J. Surg., 134:297–99 (1977), describes the use of "Vicryl" (Polyglactin 910) sutures in general surgical and cardiothoracic procedures. Absorbable meshes are often used to perform a buttressing role for soft tissue during healing, and may also act as a scaffolding system for ingrowth of connective tissue. Greisler, Arch. Surg., 117:1425–31 (1982), describes vascular grafts produced from bi-component fabrics based on Dacron and biodegradable polyester fibers. These are reported to achieve the required low bleeding porosity at implantation and high porosity during the healing stage as degradation proceeds. Tissue regeneration is promoted by tissue growth and adherence to the biodegradable scaffold provided by the graft structure.

The lactide/glycolide polymers and copolymers tend to demonstrate an easily characterized and controllable degradation rate and tend to be nontoxic, which is advantageous for manufacture of controlled release rate delivery systems for a wide variety of bioactive materials, such as pharmaceuticals. U.S. Pat. No. 4,563,489 discloses production of a biodegradable polymer delivery system for bone morphogenetic protein based on a poly (lactide co-glycolide) copolymer. Development of suitable delivery methods is important for such therapeutic proteins since they are readily absorbed by the body. Schakenraad et al., Biomaterials, 9:116–20 (1988), describe the development of a biodegradable hollow fiber of poly(L-lactide) for controlled release of contraceptive hormone.

U.S. Pat. No. 4,719,246 discloses compositions wherein segments of poly (R-lactide) interlock or interact with segments of poly (S-lactide), producing a crystalline phase having a melting point higher than that of either component. Processes are described for preparing the above compositions, e.g., by mixing and combining the previously prepared polymeric components in a suitable solvent or in the molten state and processes for preparing gels and porous structures of the compositions. The patent discloses spontaneous gel formation from solutions of blended polylactide enantiomers on stirring. It is described that porous structures are produced from gels of the composition by a process comprising solvent exchange and evaporation.

U.S. Pat. No. 4,637,931 discloses production of a bone repair material consisting of decalcified freeze-dried bone (DFDB) and biodegradable biocompatible copolymer, namely poly[L(−) lactide co-glycolide] copolymer, which is described as being used for improving and accelerating the healing of osseous tissue.

U.S. Pat. No. 4,578,384 discloses a material, consisting of a combination of a proteolipid and a biodegradable, biocompatible copolymer which is stated to facilitate improved healing of osseous wounds when implanted at the site of the broken tissue.

The methods disclosed in U.S. Pat. Nos. 4,637,931 and 4,578,384 for producing biodegradable bone repair materials from polymer solutions generally comprise the stages of polymer dissolution, polymer precipitation in a nonsolvent, partial drying of the precipitate and compaction of wet precipitate in a mold, followed by heating/drying to produce the finished implant.

U.S. Pat. No. 4,563,489 discloses a biodegradable PLA polymer delivery system for bone morphogenetic protein (BMP) to induce formation of new bone in viable tissue. The delivery composition described is substantially pure BMP in combination with a biodegradable PLA polymer, prepared by admixing the BMP with the biodegradable polymer. The composition is implanted in viable tissue where the BMP is slowly released and induces formation of new bone.

The method for preparing the implant material of U.S. Pat. No. 4,563,489 generally comprises (1) dissolving the physiologically acceptable biodegradable polymer in a solvent such as ethanol, acetone or chloroform, (2) admixing the polymer solution with BMP to form a dispersion of BMP in the polymer solution and (3) precipitating the composite by adding a second solvent which causes precipitation of the polymer or lyophilizing the dispersion or otherwise treating the dispersion to remove it from solvent and form the BMP-PL composite. After composite formation, it is filtered, pressed or otherwise processed to remove the solvent, and the resulting composite solid is formed into the desired shape for implantation. Other additives may be included, e.g., antibiotics, prosthesis devices, radio-opacifying agents.

The delivery compositions of U.S. Pat. No. 4,563,489 have relatively small masses and are used in relatively thin layers (i.e., in the range of 1 mm to 2 mm in thickness). In one example, implants are described as being shaped by pressing the wet BMP-PL precipitate in a mold to express the second solvent prior to drying. Wet (precipitated) composite was also shaped using glass molds to produce flakes, rods, films or plates. The patent also mentions that in preferred embodiments the BMP/biodegradable polymer delivery composition is formed into a dough, rod, film, flake or otherwise shaped as desired. The patent further mentions that the BMP/PL composition, while still dispersed or dissolved in solvent, may be formed into small pellets, flakes, platelets, etc., by casting in molds and allowed to dry or harden.

Several other processing techniques have been utilized for production of resorbable implants from the synthetic alpha-polyesters, such as PLA. U.S. Pat. No. 4,776,329 discloses the production of a resorbable compressing screw for use in orthopaedic surgery by injection molding. U.S. U.S. Pat. No. 4,781,183 discloses the production of surgical structural elements, such as plates or pins, consisting of bioabsorbable or semi-bioabsorbable composites. Specifically, a bone fixation device is disclosed based on an absorbable homopolymer of L-lactide or DL-lactide or a copolymer of L-lactide and a reinforcement material. Poly (L-lactide) was selected as the preferred matrix material. The reinforcement is described to be either particulate, such as hydroxyapatite or tricalcium phosphate, or fibrous, such as alumina, polyethylene terephthalate, or ultra-high modulus polyethylene.

Composite materials used for production of bone fixation devices may be manufactured by various routes. For particulate-filled systems, filler is typically added in the desired concentration to the bulk melted polymers in a stirred reactor vessel just subsequent to polymerization. Alternatively, particulate filler, such as tricalcium phosphate, may be thoroughly mixed with the melted bioabsorbable polymer under nitrogen or vacuum.

For fiber reinforced materials, solution impregnation and lamination or melt impregnation and lamination techniques are typically utilized. In the former case, fibers or woven fabric may be immersed in a solution of the biodegradable polymer in methylene chloride. The impregnated reinforcement may be dried, then laid up in a mold to a predetermined thickness. Vacuum may be applied using a vacuum bag, then heat and compression applied to consolidate the laminate.

Melt impregnation and lamination first typically require the making of films of the biodegradable polymer by solvent casting or melt processing, or the preparation of fibrous mats by running a solution of the polymer into a non-solvent in a thin stream to form a stringy precipitate. This precipitate may be pressed into a mat at room temperature. The films or mats may then be laid between yarn or fabric layers in a mold of predetermined thickness and consolidated as above.

Poly(L-lactide)/alumina fiber laminates may be produced by laying up melt-pressed poly(L-lactide) sheets and alumina fiber fabric in a mold and consolidating under heat and pressure. Poly(L-lactide)-Kevlar laminates may be made by solution impregnation and lamination. A laminate may also be formed by impregnating ½" chopped alumina fiber with poly(L-lactide) by stirring the chopped fiber in a chloroform solution of the polymer, then drying and consolidating the mixture, by hot pressing in a mold, to give a laminate containing 30% alumina by volume.

U.S. Pat. No. 4,550,449 discloses the production methods of direct machining of a high molecular weight, solid L(−) lactide polymer after removal from the reaction vessel and grinding and molding the polymer to form the desired implantable fixation device.

U.S. Pat. No. 4,645,503 discloses production of a moldable bone implant material containing approximately 65–95% hard filler particles and a binder composed of approximately 35–5% of a biocompatible, biodegradable thermoplastic polymer which has fluidic flow properties at a selected temperature at or below about 60° C. Variation in biodegradation rate via the usual routes for biodegradable polymers is described, namely, (1) adjustment of molecular weight, (2) substitution of the polymer subunit (copolymerization), (3) blending with a slower degrading polymer, or (4) increasing the surface area for hydrolysis by varying the proportion of binder and particles to provide voids or pores in the material.

It is an object of this invention to provide improved resorbable materials and methods for making such materials which address at least some of the shortcomings of the prior art.

SUMMARY OF THE INVENTION

The present invention relates broadly to resorbable materials produced by the gelation of a solution of an independently-gelling single polylactide enantiomer.

The term "single polylactide enantiomer" is an abbreviated description used herein to mean a homopolymer or copolymer of a single enantiomeric lactide (i.e. either L-lactide or D-lactide). That is, the term means a homopolymer or copolymer having substantially L-lactide or D-lactide enantiomeric monomer units in the polymer chain. Such polymers may be prepared by polymerization of a single enantiomeric lactide (i.e. either L-lactide or D-lactide). The term does not include blends of poly(D-lactide) with poly(L-lactide), nor does it include copolymers of D- and L- lactide.

The term "independently-gelling" means that the single polylactide enantiomer is capable of gelling independently of any other additions to the polymer solution. It should be understood that other materials may be added to the solution to vary certain properties (such as resorption rate or density) of the resorbable material product, but such additions are not necessary in the practice of this invention to effect gelation.

In a first broad embodiment, the present invention provides a method for making a resorbable material, comprising dissolving a single polylactide enantiomer in a solvent, such that the polymer solution is capable of gelling independently of any other additions to the solution. The polymer solution is allowed to form a gel, and the gel is dried to form the resorbable material product.

In a second broad embodiment, after the polymer solution forms a gel as described above, the solvent may be replaced/extracted with a nonsolvent, such that the polymer precipitates to form a substantially microporous material. The microporous material is then dried to form the product.

In a third broad embodiment, the drying step may comprise first partially drying the gel or microporous material, followed by extraction of the organic solvent or nonsolvent molecules with water, then complete drying.

In the second broad embodiment discussed above, the nonsolvent may be organic or it may be water. If it is organic, it may be desirable in some applications of this invention to immerse the microporous material in water before the drying step, to extract the organic nonsolvent molecules.

If desired, the polymer solution may be cast in a mold prior to the gel forming step, and the gel may be removed from the mold after the gel forming step, such that the gel substantially retains the shape of the mold. In this way, resorbable materials may be formed in desired shapes without the necessity of machine shaping.

Preferred solvents include acetone and ethyl acetate.

Preferably, the polymer is dissolved in the solvent to a concentration of from about 1 to about 10% weight/volume (w/v). More preferably, the concentration range is from about 2.5 to about 10% (w/v); most preferably, it is from about 7 to about 9% (w/v).

The preferred polymer is the homopolymer, poly(L-lactide). However, the polymer may alternatively be a copolymer of either L-lactide or D-lactide and another alpha-hydroxy acid, such as glycolide, provided that the copolymer is capable of independently gelling in solution.

In a preferred embodiment, the weight average molecular weight of the polymer is between about 50,000 and 200,000, most preferably around 100,000.

In order to alter the resorption rate or other characteristics of the product, a second material (e.g. another polymer) may be dissolved in the solvent before the gel forming step. To obtain satisfactory gelling, the ratio of the single polylactide enantiomer to the second material should be at least about 1:9, with the addition preferably being made to a solution having a concentration of at least about 2.5% (w/v) of the enantiomeric lactide polymer. Depending upon the desired properties of the final product, the second material can be selected from numerous possibilities, such as lactides, polymers of alpha-hydroxy acids, polymers of lactones, copolymers of at least one alpha-hydroxy acid, polyethylene oxides, polyurethane or copolymers containing a thermoplastic elastomer (e.g. polyether or polyester).

Alternatively or in addition, a filler material may be added to the solvent before the gel forming step.

The methods described above can be used to make resorbable materials which are much thicker than many prior art techniques based on solution processing. Resorbable materials as used in this invention can be molded to have virtually any minimum thickness desired. Thus, implant devices can be made having thickness designed for the particular application. For example, in some cases an implant having minimum thickness above about 2 mm may be desired; in other situations, thicker devices may be needed, e.g. above about 5 mm or 10 mm minimum thickness.

Other embodiments of the invention include resorbable materials prepared by the methods described above, and use of such materials as implantation devices, such as bone graft substitutes, bone fixation devices, coatings for implants, or devices for controlled release of bioactive materials. When used to form a bone graft substitute, the resorbable material may be machined with bores to achieve a honeycomb structure, facilitating bone growth through the device.

DETAILED DESCRIPTION OF PREFERRED EMBODIMENTS

Figure 2:
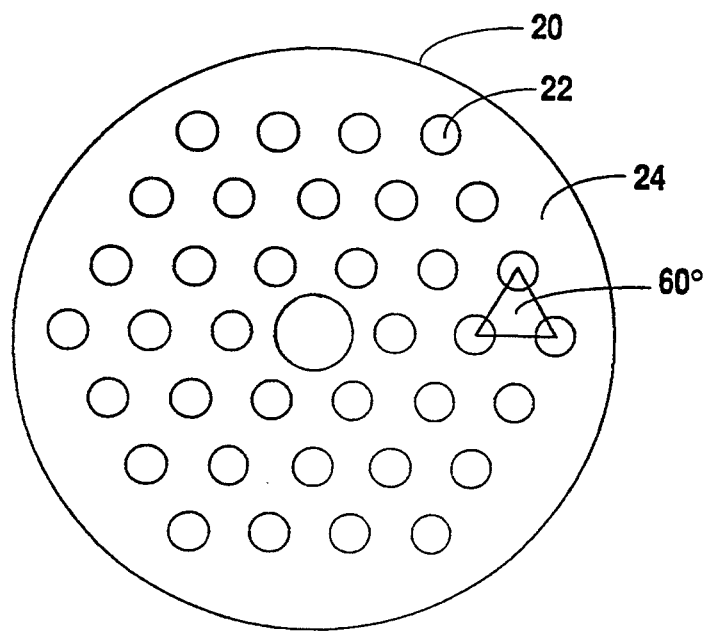
FIG. 2 is a plan view of the bone graft substitute of FIG. 1.

One preferred embodiment of the invention relates to a gel casting technique for resorbable synthetic alpha-polyesters, which may be used for producing novel bone repair materials or bone substitutes, resorbable medical implants and timed release carriers for medication. Formation of a distinct gel phase in the techniques of this invention enables production of relatively thick-section, solid moldings.

In a preferred embodiment, gel production occurs from a solution of poly(L-lactide). The polymer is selected/designed such that it is capable of gelling independently of any other polymer addition to the solution.

The gel may be used as a medium to incorporate non-gelling or weakly gelling polymers (such as low molecular weight species, non-lactide polymers, or lactide copolymers), in the material composition for control of properties such as resorption rate and density, mechanical properties, shrinkage, and thermal characteristics. Gel casting can be used to vary morphology (e.g. solid versus microporous materials) and to produce blends of homopolymers, copolymers and particulate fillers, such as tricalcium phosphate. Control of material biodegradation rate by variation of polymer type, molecular weight range, crystallinity and morphology may therefore be facilitated.

Other embodiments of the invention include processes for preparing gels from the gelling polymer and from blends of such polymer with resorbable and non-resorbable homopolymers, copolymers, and filler materials; processes for obtaining thick-section solid and microporous materials/foams from the gels; methods for controlling the shrinkage of microporous materials containing a substantial amorphous component by controlled drying and extraction of plasticizing molecules; and resorbable implants in the form of honeycomb structures for repair of long bones, being manufactured from microporous gel cast materials.

Gel casting could be extended to production of long lengths of biodegradable rod or bar by continuous casting methods, as practiced in the metalworking industries. The gel could conceivably be extruded to form filaments or fibers, avoiding a precipitation stage in the case of wet (or solution spinning) and elevated temperatures in the case of melt spinning.

It is generally known that resorbable alpha-polyester (e.g. lactide or glycolide) homopolymers or copolymers of differing molecular weight, and copolymers of differing molar ratio and sequence length, exhibit markedly different resorption rates and mechanical and thermal behavior. The gel casting technique of the present invention can provide a method for tailoring resorption rates to meet specific end use requirements in tissue repair or drug delivery.

In a preferred embodiment, the gelling medium is poly(L-lactide) (abbreviated hereinafter sometimes as "L-PLA") having an average molecular weight of around 100,000, which is sold commercially by Polysciences, Inc.

While L-PLA homopolymer is the preferred gelling medium, it should be appreciated that poly(D-lactide) homopolymer may be used. Furthermore, certain copolymers based on a single enantiomeric lactide, such as poly(L-lactide co-glycolide) can function as the gelling medium, provided that the copolymer is designed to be capable of independently gelling in solution.

Without wishing to be bound by theory, it appears that particular chain lengths or chain length distributions of the polymer facilitate production of a gel suitable for use in this invention. Specifically, the chain length distribution and structural regularity should allow the formation of effective gel junctions by crystallization and chain entanglements. Thus, if a copolymer is used as the gelling medium, it should be structured such that the L-lactide (or D-lactide) sequences have sufficient length and regularity to permit formation of stable gel junctions or network points by crystallization and by the production of effective chain entanglements. Gel junctions or network points should confer adequate gel strength for stability in the solvent swollen form and resist those forces generated by chain recoiling during the process of gel drying and shrinkage to the solid form, without destruction of the junction points.

The solvent may be acetone or ethyl acetate. Acetone is preferred since polymer dissolution is generally easier in this solvent.

Dissolution of a potential gel-forming polylactide polymer in acetone appears to be highly dependent on the physical form of the starting material. The 100,000 molecular weight poly(L-lactide) obtained from Polysciences, Inc. (Batch No. 61490) was supplied in a fine, stringy or fibrous precipitate form and dissolved readily in acetone at 52° C. Poly(L-lactide) polymer obtained from Dupont [Batch No. 59010 L051, weight average molecular weight (Mw)~100,000] was supplied in the form of solid platelets or pellets (approximately 4×15×1 mm), which were presumably produced by melt extrusion. Dissolution of the pellets was not achieved in acetone (0.4 gm in 10 cc solvent) at 52° C. in one hour and they retained their starting form without coalescing. In contrast, the Dupont material in precipitate form dissolved readily in acetone at 52° C. to produce a 4% (w/v) solution. Gelation occurred on standing at room temperature in less than 15 minutes. The poly(L-lactide) precipitate can be prepared, for example, by dissolution of 2 gm of polymer in 20 cc methylene chloride at room temperature, followed by precipitation in 40 cc methanol which is agitated by a stirrer bar. The precipitate is dried at room temperature before use.

Dissolution of the above-mentioned Dupont poly(L-lactide) in acetone was also facilitated by using the film form of the polymer. As-received pellets were converted to a film by casting a 10% (w/v) solution of the polymer in methylene chloride on a glass surface, followed by drying.

It is expected that a decrease in crystallinity of the starting polylactide will also facilitate its dissolution in acetone and increase its potential for use as a gel-forming medium.

Useful polymers and copolymers for blending with the gelling medium include lactide homopolymers, non-lactide polymers such as poly epsilon caprolactone, lactide copolymers, copolymers produced from mixtures of lactide and non-lactide comonomers such as lactones (e.g. epsilon caprolactone) or other hydroxy acids (e.g. glycolic acid), lactides, non-lactide polymers (e.g. polyethylene oxide), or copolymers containing "soft blocks" of polyether, polyester or other similar polymers. Such blending may enable variation of molecular weight distribution, density, shrinkage, and mechanical and thermal characteristics.

Useful fillers include particulates of bioceramics such as tricalcium phosphate and hydroxyapatite; nonresorbable discontinuous fibers of alumina, carbon or polyethylene terephthalate; or resorbable discontinuous fibers such as polyglycolic acid or calcium metaphosphate.

In a preferred embodiment of this invention, a method is provided for preparing solid resorbable materials, comprising the steps of:

(1) polymer dissolution in a solvent;
(2) casting the solution in a mold;
(3) gel formation in situ;
(4) removal of the shaped gel from the mold; and
(5) drying to obtain solid material in relatively thick sections.

Solid materials may alternatively be produced by extracting the solvent with a nonsolvent (e.g. methanol) over around 24 hours before drying, then drying the material. Shrinkage may result in material consolidation to form a solid core encased in a layer of microporous material. This latter material may be removed by machining if desired.

For highly crystalline polymers, e.g. polylactide, the gel casting method described above may be altered to produce microporous materials (or foams) of good structural integrity and foam consistency by following the steps (1)–(4) above, then converting the gel to a microporous material by precipitation in a nonsolvent such as methanol, followed by drying.

The density of microporous blends containing certain amorphous polymers can be controlled by predrying and water immersion subsequent to gel production. Extraction of solvent may remove the plasticizing effect of organic molecules, thereby restricting chain recoiling of the amorphous phase, which may result in material shrinkage on drying.

If substantially amorphous polymers or semi-crystalline polymers are included with the basic gelling polymer, the product gel may be converted to a microporous material by precipitation in an organic nonsolvent, and/or immersion in water to remove the plasticizing effect of organic molecules, followed by drying. Also, the extent of shrinkage and, therefore, density of microporous materials containing a substantial proportion (e.g. >about 25%) of amorphous polymer can be controlled by partially drying the gel (or the methanol-treated gel) to a desired level and extracting/replacing the solvent or nonsolvent with water prior to drying. This may remove the plasticizing effect of the organic solvent or nonsolvent molecules, which may facilitate chain recoiling in the amorphous phase, resulting in excessive shrinkage of the material on drying.

The resorption rate of biodegradable polymers may be influenced by the material form. Porosity generally facilitates fluid ingress throughout the material, exposing a large surface area of the material to chain scission by hydrolysis. Increased degradation rates can be expected. Porous implant surfaces could present a favorable surface for cell attachment and growth, enhancing its function as a biodegradable scaffold for tissue repair or implant fixation.

The release rate of medication from resorbable, polymeric delivery systems may also be influenced by the porous character and density of the delivery vehicle. The control of density and, therefore, pore size and structure in resorbable polymers may be achieved by the above-described drying/water treatment stage in the process of manufacture of microporous materials from blends containing an amorphous polymeric component.

The resulting solid or microporous materials can be used to form implantable devices of various shapes, e.g. a disc for nonunion fractures or a cylinder for repair of segmental defects. The advantages of a microporous material include the increase in surface area for hydrolysis or breakdown of the implant and the presence of a potentially better surface for attachment of osteoprogenitor cells.

Figure 1:
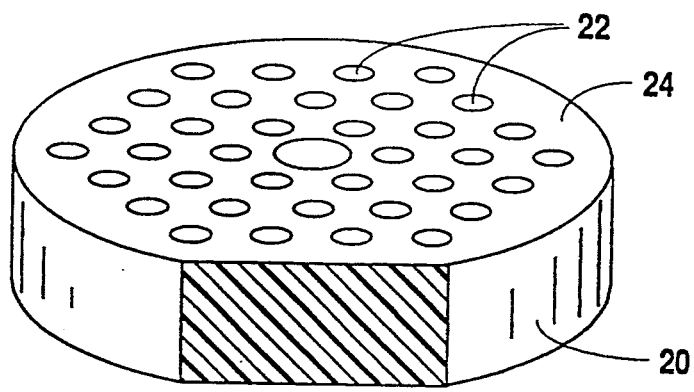
FIG. 1 is a perspective view of a honeycomb bone graft substitute made of a resorbable material provided by this invention.

As illustrated in FIGS. 1 and 2, the material can be machined to produce a bone graft substitute 20 of macroporous character, for example by drilling 100–500 $\mu$m bores 22 running the length of the implant and intersecting with the implant end surfaces 24. In a preferred embodiment, the macropores are about 500 $\mu$m in diameter, based on a hole center spacing of 1 mm. In repair of long bones, the macropores may allow marrow migration throughout the implant to establish a supply of osetoprogenitor cells and growth factor and allow primary bone growth along the pore channels. Gradual resorption of the implant bridge may allow secondary bone formations to be established and bone remodeling to take place by load transfer to the ingrown tissue. A polymer blend of slow resorbing polymer (L-PLA) and fast resorbing polymer [e.g. poly(DL-lactide co-glycolide)] can be used to produce an "enduring scaffold" system which provides a support element for immature bone formations during and after resorption of the fast degrading phase to promote and encourage satisfactory tissue repair, stability and remodeling.

EXAMPLES

The following examples are designed to illustrate certain aspects of the present invention. The examples are not intended to be comprehensive of all features and all embodiments of the present invention, and should not be construed as limiting the claims presented herein.

Material shrinkage was measured with respect to the diameter of the gel on demold. Material density was estimated from measurements of the dimensions of a disc of material and its corresponding weight in air. Drying of materials was carried out in air under ambient conditions unless otherwise specified. Polymer dissolution was aided by stirring with a magnetic stirrer bar and, unless otherwise specified, the mold was a 10cc plastic syringe body.

EXAMPLE 1

A single component gel was produced by heating finely divided L-PLA (Polysciences, Inc., Mw 100,000, Batch No. 61490) in acetone at a concentration of 7–9% (w/v), with agitation at a temperature of 46°–52° C., until dissolved (approximately 15 minutes). 7% (w/v) gave the best results.

The clear solution was poured into a mold and allowed to cool to room temperature under quiescent conditions. The cloud point, or the point at which opacity developed in solution due to crystal formation, was accompanied by a marked increase in solution viscosity, and occurred at approximately 28°–32° C. for a 10% (w/v) solution. A weak gel was formed at 25° C., which was easily disrupted by stirring. The product gel which formed in situ in the mold had a distinct white color and hardened over time. It was firm enough to withstand demold after 30 minutes at room temperature (22°–24° C.). At that point, the demolded gel was allowed to dry to remove the solvent and produce solid material. A shrinkage in diameter of approximately 50% relative to the demolded gel occurred after 24 hours air drying.

EXAMPLE 2

A demolded gel prepared as in Example 1 was immersed in methanol to extract solvent and produce a microporous material on subsequent drying.

An acetone-based gel produced from a 7% (w/v) solution was immersed in methanol for three days (50 cc methanol in 100 cc beaker with a change of immersion medium at 24 hours). The methanol was allowed to evaporate and the material allowed to dry in the beaker over four days at room temperature. A shrinkage of approximately 40% occurred relative to the gel on demold and a density of 0.36 gm/cm$^3$ was obtained for the product foam/microporous material. Treatment of the demolded gel in methanol for three days, followed by water immersion for three days, with a change in immersion medium after 24 hours, slightly reduced the shrinkage to 37% and yielded a microporous material density of 0.33 gm/cm$^3$ after drying for four days at room temperature.

An acetone-based gel of the preferred L-PLA polymer produced from a 7% (w/v) solution was redissolved by heating in an excess of solvent (e.g. 1.1 gm gel in 10 cc acetone) at 50° C. in less than ten minutes.

EXAMPLE 3

A 2.5% (w/v) solution of L-PLA (Mw 100,000) in acetone was produced by dissolving 0.5 gm of the polymer in 20 cc of solvent at 50° C. The solution was poured into molds. On standing at room temperature, opacity developed in solution after 45 minutes, denoting crystal formation. On demold after 19 hours, a strong, white gel was evident, which exhibited a 65% shrinkage in diameter after five hours air drying at room temperature.

EXAMPLE 4

L-PLA of molecular weight 200,000 (Polysciences, Inc.), when heated in acetone at 50° C. at a concentration of 2 gm polymer to 20 cc of solvent, did not dissolve completely. Instead, a milky suspension of powder in solvent was obtained. A weak gel was, however, formed from this suspension after one hour at room temperature, presumably due to dissolution of a certain fraction of the starting polymer. This same polymer dissolved readily in p-dioxane to give a 10% (w/v) solution, but did not gel under quiescent conditions at room temperature. L-PLA, with a weight average molecular weight of 50,000 (Polysciences, Inc.) when heated in acetone at a 9% (w/v) concentration also resulted in incomplete dissolution (milkiness persisted). After standing at room temperature for 17 hours, a very weak, easily damaged gel was evident on demold which collapsed under its own weight. Doubling the concentration of 50,000 L-PLA in acetone also produced a weak gel on standing which cracked or crumbled on drying.

EXAMPLE 5

The preferred polymer for the gelling medium (L-PLA, Mw 100,000) exhibited a crystalline melting point at approximately 160° C. Rapid cooling in the molten state from 230° C. resulted in increasing amorphous content, evidenced by the absence of a recrystallizing transition on cooling. On reheating, no recrystallization of the amorphous component occurred.

In contrast, a weakly gelling lactide polymer (Mw 50,000), which was substantially unsuitable for use, exhibited a recrystallizing transition at around 125° C., followed by a crystalline melting transition at 170° C. on reheating the amorphous form produced by rapid cooling. This reflected a greater chain mobility for this polymer.

These tests suggest that operable semi-crystalline polymers suitable for producing the gelling medium in the disclosed gel casting technique may be characterized by a limited chain mobility due to molecular weight distribution, which impedes recrystallization of the amorphous form of the polymer on heating.

EXAMPLE 6

Formation of a distinct gel phase immediately following polymer dissolution tends to enable production of thick solid moldings.

An 11 mm diameter cylinder of the preferred L-PLA was produced by air drying for 17 hours a gel produced from a 9% (w/v) solution in acetone, followed by annealing for 56 hours at 72° C. Final shrinkage (diameter) was 62%. In contrast, the absence of gelation in a 7% (w/v) solution of the preferred L-PLA polymer in chloroform at room temperature resulted in the formation of a film or coating on the mold walls on solvent evaporation over four days.

Shrinkage forces developed during drying of the gel at room temperature yielded a homogenous, thick-section solid product with a state of consolidation visually similar to that of a thermoplastic processed in the melt at high temperatures and pressures by injection molding or extrusion. Material consolidation in gel casting was achieved in a "cold" system through a combination of factors. The gel's liquid medium provided crystal mobility and chain flexibility in the amorphous phase by a plasticizing effect. This, coupled with the forces generated by the tendency of macromolecules in the solvent-swollen, amorphous phase to recoil on evaporation of the swelling medium, resulted in the observed good material consistency.

EXAMPLE 7

An 11% (w/v) solution of low molecular weight L-PLA (Mw 2000, Polysciences, Inc.) was produced by dissolving 2.2 gm polymer in 20 cc acetone at 52° C. and allowed to stand at room temperature for 21 hours. An extremely weak gel was evident on demold, which did not retain the molded form but collapsed under its own weight, eventually drying to a weak, brittle solid.

12% (w/v) solutions in acetone of poly(DL-lactic acid) [Mw 20,000, Polysciences, Inc.] or 70:30 poly(DL-lactide co-glycolide) copolymer [Mw 30–60,000, Polysciences, Inc.] or 90:10 poly(DL-lactide co-glycolide) copolymer [Mw 30–60,000, Polysciences, Inc.] or 85:15 poly(DL-lactide co-glycolide) copolymer [Mw 40–100,000, Dupont] did not gel on standing at room temperature. Gradual evaporation of solvent occurred from the bulk solution, resulting in formation of a viscous fluid.

These polymers were combined with the preferred gelling L-PLA polymer, for example, in the ratio 25 (L-PLA):75 (other), by simultaneous dissolution in acetone to produce a blended polymer gel. The gel was subsequently converted to a solid material by drying/solvent extraction. For predominantly crystalline polymer additions, e.g. lower molecular weight L-PLA, the gel was converted to a microporous material by precipitation in a nonsolvent, followed by drying. For substantially amorphous polymer additions to the basic gelling polymer, the gel was converted to a microporous material by precipitation in a nonsolvent and/or immersion in water (to remove the plasticizing effect of organic molecules), followed by drying. Non-gelling or weakly gelling polymers were incorporated into a particular material composition by using L-PLA as the gelling medium.

EXAMPLE 8

A 30% solid, particulate-filled, resorbable material consisting of tricalcium phosphate in L-PLA was produced by dissolving 1.4 gm L-PLA (Mw 100,000) in 20 cc acetone at 52° C. On dissolution of the polymer (in approximately 15 minutes), 0.6 gm of tricalcium phosphate (TCP) [J. T. Baker] was added, with stirring until a uniform dispersion was obtained. The suspension was poured into a mold and allowed to stand at room temperature. A strong, firm gel was obtained on demold after 1½ hours, which exhibited a shrinkage value of 55% over 29 hours air drying to yield a solid, particulate-filled material having a density of 1.02 gm/cm$^3$.

An acetone-based gel of TCP-filled, L-PLA, produced as described above, was immersed in methanol on demold for five days, then air dried for four days. The microporous material obtained exhibited a shrinkage of 26% and a density of 0.27 gm/cm$^3$.

EXAMPLE 9

A 29% TCP particulate-filled microporous blend of L-PLA with 70:30 poly(DL-lactide co-glycolide) copolymer [Mw 30–60,000, Polysciences, Inc.] was produced by dissolving 0.8 gm and 2.4 gm of each polymer, respectively, in 20 cc acetone at 52° C. Particulate filler (1.28 gm) was dispersed in the solution by stirring. The suspension was transferred to molds and allowed to stand at room temperature for 22 hours before demold, whereupon a weak, sticky gel was obtained. (Sedimentation of TCP filler was limited prior to gel formation by the viscosity of the blended polymer solution.) The gel was subsequently immersed in 50 cc methanol in a 100 cc beaker for two days with a solvent change at 24 hours. The nonsolvent was then allowed to evaporate and the material allowed to dry in the beaker over three days. The TCP particulate-filled L-PLA:PLG microporous blend obtained exhibited a shrinkage of 28% and a density of 0.6 gm/cm$^3$.

EXAMPLE 10

Solid L-PLA material (Mw 100,000, Polysciences, Inc.) was produced by dissolving 1.8 gm of this preferred gelling polymer in 20 cc acetone at 52° C. The solution was transferred to cylindrical molds and allowed to stand at room temperature. The gel obtained on demold after 39 minutes was air dried under ambient conditions to consolidate the polymer as a solid rod. Thermal transitions were determined by Differential Scanning Calorimetry (DSC). On heating at 20° C./min., from 10° C. to 230° C., a single melting peak was observed at 159° C. No recrystallization peak was evident on immediate cooling of the sample at 50° C./min. to 10° C. Reheating the sample at 50° C./min to 230° C. revealed only a glass transition (Tg) at 70° C., indicating that the polymer exists mainly in the amorphous phase after rapid cooling from the melt.

EXAMPLE 11

A 50:50 blend of L-PLA (Mw 100,000) and poly(DL-lactide) [Mw 20,000, Polysciences, Inc.] was produced by codissolving 1 gm of each polymer in 20 cc acetone at 52° C. The solution was poured into cylindrical plastic molds and allowed to stand at room temperature. The product blended gel was demolded after 55 minutes and air dried to consolidate the material as a solid rod. Thermal transitions were revealed by DSC, using the test procedure described in Example 10. A broad, spiky melting peak was observed on heating, extending from 120°–160° C. and centered around 140° C. No recrystallization peak was evident on cooling the sample. A glass transition was observed on remelting at 53° C.

The (DL-lactide) polymer showed a glass transition at 35° C. on heating, which shifted to 45° C. after cooling from 230° C. and reheating.

EXAMPLE 12

A 25:75 blended solution of high molecular weight L-PLA (Mw 100,000) and low molecular weight L-PLA (Mw 2,000, Polysciences, Inc.) was produced by dissolving 0.6 gm and 1.8 gm of each polymer, respectively, in 20 cc acetone at 50° C. The solution was transferred to molds and allowed to stand at room temperature. The resultant firm gel was demolded in 30 minutes, following a rapid cloud point of five minutes. Air drying the gel over five days resulted in a shrinkage of 44% and production of a hard, waxy solid. A 25:75 blended gel of high and low molecular weight L-PLA, demolded after 19 hours, was immersed in 50 cc methanol in a 100 cc beaker for two days with a change of medium after 24 hours. The methanol was allowed to evaporate and the material allowed to dry in the beaker over four days at room temperature. The blended, microporous material obtained exhibited a shrinkage of 19% and a density of 0.29 to 0.43 gm/cm$^3$.

The thermal testing procedure described in Example 10 revealed melting peaks at 136° C. and 155° C. for 25:75 microporous material, roughly corresponding to the individual homopolymer components, and no recrystallizing transition on cooling. On reheating, a glass transition was observed at 63° C., a broad recrystallizing transition at 130° C. and a melting peak at 155° C. Solid, low molecular weight L-PLA obtained by air drying the weak gel produced from an 11% (w/v) solution in acetone revealed low broad melting peaks centered around 104° C. and 118° C. and the main melting peak at 140° C. No recrystallization transition was observed on cooling. On reheating, a glass transition was evident at 50° C. and a small melting peak at 143° C.

The lower molecular weight polymer species introduced into the blend allowed sufficient chain mobility for recrystallization to occur from the amorphous form on heating. Recrystallization did not occur for the amorphous form of the single higher molecular weight polymer.

It may be possible to vary the crystallinity of a blend by isothermal conditioning.

EXAMPLE 13

A 25:75 blended solution of L-PLA and a 70:30 poly(DL-lactide co-glycolide) copolymer [Mw 30–60,000, Polysciences, Inc.] was produced by co-dissolution of 0.6 and 1.8 gm of each polymer, respectively, in 20 cc of acetone at 52° C. The solution was transferred to molds and allowed to stand at room temperature. An acetone seal was applied to the gel after one hour to prevent surface drying at long demold times. The blended gel produced on demold after 21 hours was subsequently immersed in methanol for four days, 18 hours before drying at room temperature for one week. Shrinkage of the methanol-based material occurred on drying to the extent of 48%, to yield a practically solid polymer core. An acetone-based gel was immersed in methanol for five days, 18 hours, then immersed in water for 21 hours prior to drying. In this case, the microporous blend obtained exhibited a shrinkage of only 13% and a density of 0.25 gm/cm$^3$.

The density of microporous materials could be varied by water treatment subsequent to acetone extraction in methanol. Extraction of organic liquid from the material and its substitution by water removed the plasticizing effect of the organic molecules, raised the Tg and thereby restricted chain recoiling of the amorphous phase, which resulted in material shrinkage on drying.

25:75 acetone-based gels of L-PLA and 70:30 poly(DL-lactide co-glycolide) were demolded after 24 hours and immersed in methanol (50 cc methanol in 100 cc beaker) for three days, with a change of immersion medium at 24 hours. Samples were then air dried for time periods of 0, 60 and 80 minutes before immersion in water for three days, with a change in immersion medium at 24 hours. Samples were finally air dried under ambient conditions for three days to give uniformly microporous materials with the final shrinkage and density values shown in Table 1.

TABLE 1

| Air drying time (minutes) prior to water immersion | 0 | 60 | 80 |
|---|---|---|---|
| Final foam shrinkage (%) | 5 | 15 | 19 |
| Foam density (gm/cm$^3$) | 0.19 | 0.22 | 0.29 |

EXAMPLE 14

A 25:75 blended solution of L-PLA and 85:15 poly(DL-lactic co-glycolide) [Mw 40–100,000, Dupont] was produced by dissolution of 0.8 gm and 2.4 gm of each polymer, respectively, in 20 cc acetone at 52° C. The solution was transferred to molds and allowed to stand at room temperature. A cloud point was observed after approximately 15 minutes. On demold after 24 hours, gel samples were air dried for time periods of 0, 15, 45, and 75 minutes before immersion in water for three days, with a change of immersion medium after 48 hours. Drying of the microporous materials resulted in the final shrinkage and density values shown in Table 2, with foam properties ranging from tough and pliable to hard-yet-tough as density increased with predry time.

TABLE 2

| Air drying time (minutes) prior to water immersion | 0 | 15 | 45 | 75 |
|---|---|---|---|---|
| Final foam shrinkage (%) | 8 | 10 | 17 | 20 |
| Foam density (gm/cm$^3$) | 0.22 | 0.25 | 0.32 | 0.38 |

EXAMPLE 15

Poly(DL-lactide) [Mw 40–100,000, Dupont] was dissolved in acetone to produce a 12% (w/v) solution, transferred to a 10 cc syringe body and allowed to stand at room temperature. Gelation did not result and solvent evaporation occurred over seven days, to leave a coating on the mold walls. A 25:75 blended solution of L.PLA and poly(DL-lactide) was produced by co-dissolution of 0.8 gm and 2.4 gm of each polymer, respectively, in 20 cc acetone at 52° C. The solution was transferred to molds and allowed to stand at room temperature. A cloud point was observed after approximately 10 minutes. An acetone seal was applied to the gel after 30 minutes to prevent surface drying at long demold times. On demold after 21 hours, a soft gel was obtained, which was immersed in methanol for three days with a change of immersion medium after 22 hours. Immersion of the methanol-based material for three days in water, with a change in medium after 24 hours, prior to air drying resulted in a white, microporous material which exhibited a shrinkage of 1% and a density of 0.18 gm/cm$^3$.

On demold after 21 hours, an acetone-based gel sample was air dried for 65 minutes before immersion in water for three days, with a change of immersion medium after 24 hours. Drying of the microporous material so obtained resulted in a final shrinkage of 26% and a density of 0.40 qm/cm$^3$.

L.PLA can be used as a gelling medium to incorporate non-gelling polymers in a particular material composition for adjustment of resorption rates, for example.

EXAMPLE 16

A 50:50 blended solution of L-PLA and low molecular weight polycaprolactone (Mw 15,000, Polysciences, Inc.) was prepared by co-dissolution of 0.7 gm of each polymer in 10 cc acetone at 52° C. The solution was transferred to a mold and allowed to stand at room temperature. A cloud point was observed after 30 minutes. A firm, white damage-tolerant gel was obtained on demold after 25 hours, which was immersed in methanol for two days, 21 hours. Drying of this methanol-based material at room temperature for two days, 19 hours resulted in a shrinkage of 30% and a density of 0.45 gm/cm$^3$ for the resulting firm, white, microporous material.

Treatment of the methanol-based material in a 50% methanol/water mixture for two days, 19 hours, then water for six days prior to air drying for four days resulted in a microporous material which exhibited a shrinkage of 15% relative to the demolded gel and a density of 0.26–0.29 gm/cm$^3$. DSC revealed melting transitions at 64° C. and 160° C., corresponding to the individual blend components.

EXAMPLE 17

A 50:50 blended solution of L-PLA (Mw 100,000 Polysciences, Inc.) and DL-lactide [Mw 144.12, Polysciences, Inc.) was prepared by co-dissolution of 0.7 gm of each material in acetone at 52° C. The solution was transferred to a cylindrical mold and allowed to stand at room temperature. An acetone seal was applied after 30 minutes. A firm, white, damage-tolerant gel was obtained on demold after 24 hours, which was immersed in methanol for two days, 21 hours. Drying of this methanol-based material for two days, 19 hours resulted in a hard, white microporous material exhibiting a shrinkage of 37% relative to the demolded gel and a density of 0.38 gm/cm$^3$. Treatment of the methanol-based material for two days, 19 hours in a 50% methanol/water mixture, followed by immersion in water for six days, prior to air drying (four days), resulted in a firm, white microporous material which exhibited a shrinkage of 19% and a density of 0.16 gm/cm$^3$. DSC revealed a small melting peak at 60° C. and the main melting transition at 160° C.

EXAMPLE 18

A bone repair device potentially suitable for general bone augmentation and reconstruction or for repairing large segmental defects and nonunion fractures was fabricated from a microporous 25:75 blend of L-PLA and 85:15 poly(DL-lactide co-glycolide) produced by the disclosed gel casting technique.

0.6 gm of L-PLA (Mw 100,000) and 1.8 gm of 85:15 poly(DL-lactide co-glycolide) copolymer (Medisorb, Mw 40–100,000, Dupont) were dissolved with stirring in 20 cc acetone at 52° C. in approximately 15 minutes. The solution was transferred to molds and allowed to stand at room temperature for 24 hours before demold. The gel obtained was dried in air for 45 minutes to give a shrinkage of 19%, then immersed in water for three days, with a change in immersion medium after 24 hours. Air drying of the microporous material obtained over four days resulted in a final shrinkage of 17% and a density of 0.32 gm/cm$^3$. This stock material was machined further to produce a particular honeycomb design for repair of long bones.

The instant invention has been disclosed in connection with specific embodiments. However, it will be apparent to those skilled in the art that variations from the illustrated embodiments may be undertaken without departing the spirit and scope of the invention.

What is claimed is:

1. A resorable implantation device comprising a dried gel, the dried gel being formed from cooling a polymer solution comprising an independently-gelling polymer of a single enantiomeric lactide dissolved in a solvent to form a gel capable of substantially retaining a molded shape upon handling thereof, and drying the gel to form the resorbable implantation device.

2. A resorbable implantation device comprising a dried microporous material, the dried microporous material being formed from cooling a polymer solution comprising an independently-gelling polymer of a single enantiomeric lactide dissolved in a solvent to form a gel capable of substantially retaining a molded shape upon handling thereof, extracting the solvent with a nonsolvent to precipitate out the microporous material, and drying the microporous material to form the resorbable implantation device.

3. The resorbable implantation device of claim 1 which includes a second material incorporated within the dried gel.

4. The resorbable implantation device of claim 2 which includes a second material incorporated within the dried microporous material.

5. The resorbable implantation device of claim 3 or 4, wherein the second material comprises a polymer.

6. The resorbable implantation device of claim 5, wherein the second polymer comprises a polymer of an alpha-hydroxy acid, a polymer of a lactone, a copolymer of at least one alpha-hydroxy acid, a polyethylene oxide, or a copolymer containing a thermoplastic elastomer.

7. The resorbable implantation device of claim 1 which includes a filler material incorporated within the dried gel.

8. The resorbable implantation device of claim 2 which includes a filler material incorporated within the dried microporous material.

9. The resorbable implantation device of claim 1 or 2, wherein the single enantiomeric lactide is L-lactide.

10. The resorbable implantation device of claim 1 or 2, wherein the polymer is poly(L-lactide).

11. The resorbable implantation device of claim 1 or 2, wherein the single enantiomeric lactide is D-lactide.

12. The resorbable implantation device of claim 1 or 2, wherein the polymer is poly(D-lactide).

13. The resorbable implantation device of claim 1 or 2 which has a minimum thickness of at least about 2 mm.

14. The resorbable implantation device of claim 1 or 2 which has a minimum thickness of at least about 5 mm.

15. The resorbable implantation device of claim 1 or 2 which has a minimum thickness of at least about 10 mm.

16. The resorbable implantation device of claim 1 or 2 which has a honeycomb structure.

17. The resorbable implantation device of claim 1 or 2, wherein the solvent is acetone or ethyl acetate.

18. The resorable implantation device of claim 1 or 2 which includes at least one bore therein.

19. The resorable implantation device of claim 1 or 2 which includes a bioactive material incorporated therein.

* * * * *